US010478124B2

(12) United States Patent
An et al.

(10) Patent No.: US 10,478,124 B2
(45) Date of Patent: Nov. 19, 2019

(54) PRESSURE SENSOR TO DETECT BODY SOUNDS

(71) Applicant: Cardiac Pacemakers, Inc., St. Paul, MN (US)

(72) Inventors: Qi An, Blaine, MN (US); Yinghong Yu, Shoreview, MN (US); Jeffrey E. Stahmann, Ramsey, MN (US); Pramodsingh Hirasingh Thakur, Woodbury, MN (US); Michael J. Kane, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 138 days.

(21) Appl. No.: 15/654,838

(22) Filed: Jul. 20, 2017

(65) Prior Publication Data

US 2018/0020983 A1    Jan. 25, 2018

Related U.S. Application Data

(60) Provisional application No. 62/364,740, filed on Jul. 20, 2016.

(51) Int. Cl.
| | | |
|---|---|---|
| *A61B 5/00* | (2006.01) | |
| *A61B 5/021* | (2006.01) | |
| *A61B 5/0285* | (2006.01) | |
| *A61B 7/00* | (2006.01) | |
| *A61B 5/0205* | (2006.01) | |
| *A61B 5/02* | (2006.01) | |
| *A61B 7/04* | (2006.01) | |

(52) U.S. Cl.
CPC ............ *A61B 5/6843* (2013.01); *A61B 5/021* (2013.01); *A61B 5/0205* (2013.01); *A61B 5/0285* (2013.01); *A61B 5/686* (2013.01); *A61B 7/00* (2013.01); *A61B 7/003* (2013.01); *A61B 5/02028* (2013.01); *A61B 7/04* (2013.01); *A61B 2562/0247* (2013.01)

(58) Field of Classification Search
CPC ..... A61B 5/6843; A61B 5/0205; A61B 5/021; A61B 5/686; A61B 7/00; A61B 7/003; A61B 2562/0247
See application file for complete search history.

(56) References Cited

U.S. PATENT DOCUMENTS

| | | |
|---|---|---|
| 5,913,826 A | 6/1999 | Blank |
| 2008/0171941 A1 | 7/2008 | Huelskamp et al. |
| 2012/0172891 A1 | 7/2012 | Lee |
| 2013/0060149 A1 | 3/2013 | Song et al. |

(Continued)

FOREIGN PATENT DOCUMENTS

| | | |
|---|---|---|
| CN | 109600987 A | 4/2019 |
| WO | WO-2018017796 A1 | 1/2018 |

OTHER PUBLICATIONS

"International Application Serial No. PCT/US2017/043004, International Preliminary Report on Patentability dated Jan. 21, 2019", 8 pgs.

(Continued)

*Primary Examiner* — Paula J Stice
(74) *Attorney, Agent, or Firm* — Schwegman Lundberg & Woessner, P.A.

(57) ABSTRACT

This document discusses, among other things, using a pressure sensor to detect body sound information of a patient, such as cardiac murmurs, respiratory sounds, etc.

20 Claims, 3 Drawing Sheets

(56) References Cited

U.S. PATENT DOCUMENTS

2015/0174413 A1   6/2015   Stahmann et al.
2015/0224320 A1   8/2015   Stahmann

OTHER PUBLICATIONS

"International Application Serial No. PCT/US2017/043004, International Search Report dated Nov. 2, 2017", 5 pgs.
"International Application Serial No. PCT/US2017/043004, Written Opinion dated Nov. 2, 2017", 6 pgs.

PRESSURE SENSOR TO DETECT BODY SOUNDS

CLAIM OF PRIORITY

This application claims the benefit of priority under 35 U.S.C. § 119(e) of U.S. Provisional Patent Application Ser. No. 62/364,740, filed on Jul. 20, 2016, which is herein incorporated by reference in its entirety.

TECHNICAL FIELD

This document relates generally to implantable medical devices, and more particularly, but not by way of limitation, to systems, devices, and methods to detect body sounds using a pressure sensor.

BACKGROUND

Implantable medical devices, such as cardiac rhythm management (CRM) devices, can be used to monitor, detect, or treat various cardiac conditions that can result in a reduced ability of a heart to sufficiently deliver blood to a body. In some cases, heart conditions may lead to rapid, irregular, or inefficient heart contractions, etc. To alleviate one or more of these conditions, various medical devices can be implanted in a patient's body to monitor heart activity or to provide electrical stimulation to optimize or control contractions of the heart.

Traditional cardiac rhythm management (CRM) devices, such as pacemakers or defibrillators, include subcutaneous devices implanted in a chest of a patient, having one or more leads to position one or more electrodes or other sensors at various locations in the heart, such as in one or more of the atria or ventricles. In certain examples, the one or more leads can include a pressure sensor positioned in the heart and coupled to the CRM device through a conductor in the lead. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

For example, the CRM device or the one or more leads can include an acoustic sensor, such as an accelerometer, a microphone, or one or more other acoustic sensors configured to detect body sounds from a patient, such as cardiac murmurs, respiratory sounds, heart sounds, mitral regurgitation, mitral stenosis, or other body sounds. The body sounds, or other physiologic information, can be used to diagnose one or more physiologic conditions, provide an alert, or to control one or more therapies.

However, implantable CRM devices typically require an incision in the chest to implant the device in a pocket under the skin, which, in certain examples, can become infected, reduce mobility near the implant site, migrate, or leave a scar or lump where the device is implanted. Further, leads positioned in the heart may cause complications, becoming dislodged, breaking, migrating, or even perforating the heart.

Leadless cardiac pacemakers (LCP) have developed that can detect physiologic information from or provide one or more therapies or stimulation to the heart without traditional lead or implantable CRM device complications. Such LCP devices are typically small, self-contained devices (e.g., smaller than traditional implantable CRM devices), and in certain examples, having more limited power and processing capabilities than a traditional CRM device.

In certain examples, multiple LCP devices can be implanted in the heart to detect physiologic information from, or provide one or more therapies or stimulation to, one or more chambers of the heart. The multiple LCP devices can communicate between themselves, or one or more other implanted or external devices.

SUMMARY

This document discusses, among other things, using a pressure sensor to detect body sound information of a patient such as, for example, cardiac murmurs, respiratory sounds, mitral regurgitation, mitral stenosis, etc.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
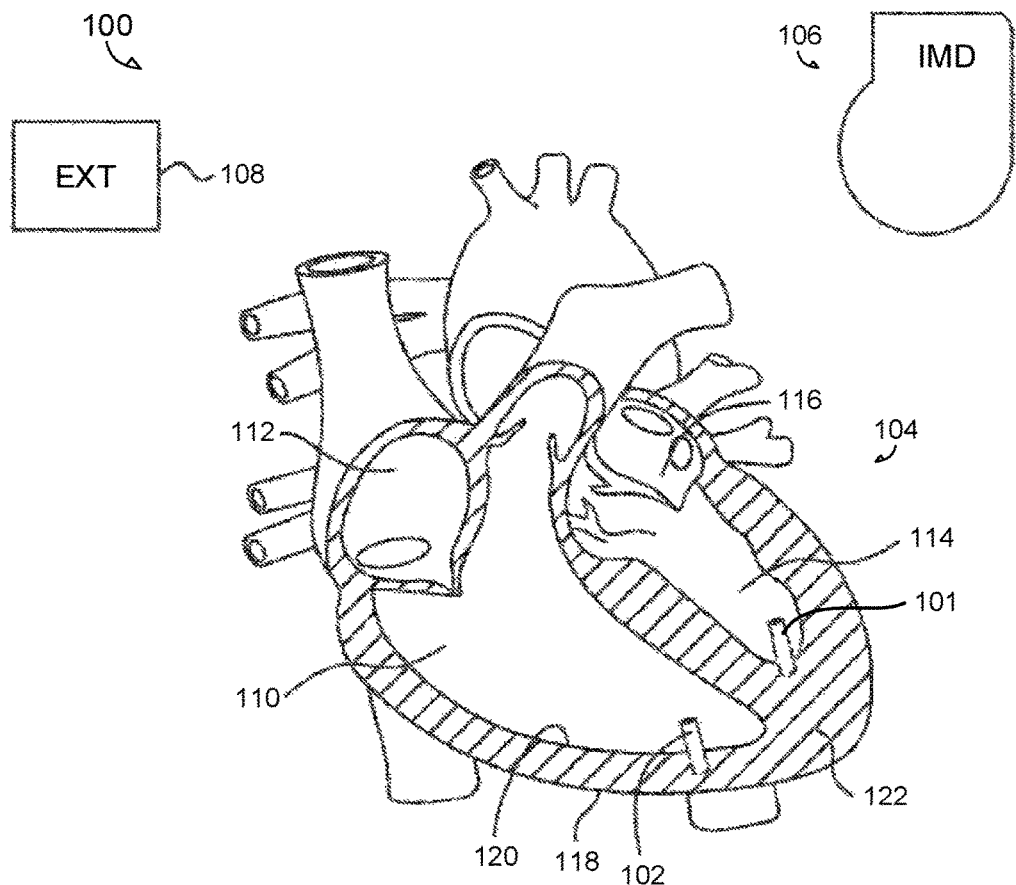
FIG. 1 illustrates generally an example system including first and second leadless cardiac pacemakers (LCP) devices positioned in left and right ventricles of a heart, respectively.

The present inventors have recognized, among other things, that a pressure sensor, in addition to detecting a pressure signal, can be used to detect body sounds of a patient from within an atrium or a ventricle of the heart. Detection of such body sounds using the pressure sensor, as described below, can be used to improve operation or programming of a medical device including or coupled to such pressure sensor.

The pressure sensor can include a pressure transducer or one or more other pressure sensors, such as a pressure sensor in a leadless cardiac pacemaker (LCP), a pressure sensor on an implantable lead, or a pressure sensor in one or more other implantable or insertable medical devices, configured to be positioned in one or more of an atria or a ventricle of a heart, such as a left ventricle (LV), or on or near the heart, such as in a pulmonary artery, to detect a pressure signal. In an example, the pressure transducer can include a deformable element proximate a rigid element. Each of the deformable and rigid elements can include a conductive surface, such that movement of the deformable surface can be sensed in relation to the rigid element, for example, using a change in capacitance. In other examples, the pressure sensor can include a deformable material, which, when deformed, such as by a change in pressure, can alter a property (e.g., a resistance, an inductance, a capacitance, etc.) of the deformable material. In other examples, one or more other pressure sensors can be used.

In contrast to cardiac pressures, body sounds typically have much higher signal frequencies and lower energy values than cardiac pressure signals. In an example, a pressure sensor in the left ventricle of a leadless pacemaker system can detect low-frequency measurements (e.g., 10-20 Hz) indicative of changes in the pressure of the left ventricle, whereas body sounds can include cardiac murmurs (e.g., 100-500 Hz) or respiratory sounds (e.g., 1-2 kHz), including wheezes, rhonchi, crackles, etc. In certain examples, certain respiratory sounds can have useful information at a range of frequencies lower than 1-2 kHz (e.g., down to 40 Hz, etc.). In other examples, body sounds can include heart sounds having information at a range of frequencies (e.g., 5-90 Hz) at least partially overlapping with the low-frequency measurements. In such examples, however, it can be beneficial to focus on the higher frequencies, or to detect the overlapping frequencies during specific portions of the low-frequency measurements (e.g., pressure at 10-20 Hz, etc.) to optimize detection of heart sounds with the pressure sensor.

Typically, lower frequency, higher amplitude physiologic information is cheaper and easier to detect (e.g., low sampling rate, resolution, complexity, etc.) than higher frequency, lower amplitude physiologic information. With lower frequency information, less sampling is required, and with higher signal amplitude or variation, less resolution is required to detect changes. Further, in certain examples, a system including the pressure sensor, such as an LCP device or one or more other implantable or insertable medical devices, can include different acoustic sensors (e.g., accelerometers, a microphones, etc.) capable of detecting body sounds with higher accuracy than the pressure sensor. However, additional sensors require additional cost, complexity, power usage, or size in a small-form LCP or other implantable or insertable medical device. Accordingly, even though additional acoustic sensors may better detect body sounds, it can be advantageous to use existing, low-cost, multi-use sensors, such as the pressure sensor, to detect other physiologic information from the patient without substantially increasing the size, cost, or power usage of the device.

For example, the device can require more processing power to detect body sounds in noisy environment, or in the presence of other signals, in contrast to a more quiet environment. Accordingly, the present inventors have recognized, among other things, that the pressure sensor, one or more electrodes, or one or more secondary sensors can detect physiologic conditions under which the pressure sensor can better detect body sounds (e.g., in the presence of less noise, in conditions optimized to detect certain physiologic information, etc.). For example, the pressure in the left ventricle is low during diastole. Accordingly, to enhance detection of body sounds, such as respiratory sounds, the pressure sensor can be gated using information about the heart cycle, for example, that the heart is in diastole. Similarly, in other examples, to enhance detection of other body sounds, such as mitral stenosis, mitral regurgitation, or one or more other sounds associated with the opening or closing of respective heart valves (depending on the placement of the LCP or other implantable or insertable medical device), the pressure sensor can be gated using information that the heart is in systole.

Other physiologic information can be used to gate the pressure sensor, depending on desired body sounds, such as pressure (e.g., when the information from the pressure sensor indicates that the pressure is below a threshold), respiration phase (e.g., body sounds can be detected using the pressure sensor during at least a portion of at least one of inspiration or expiration), patient posture (e.g., body sounds can be detected using the pressure sensor while the patient is lying in a specific position, arm overhead, etc.), activity (e.g., body sounds can be detected during or after a period of activity, etc.), heart rate (e.g., body sounds can be detected when the heart rate increases or decreases, etc.), respiration rate, etc.

In certain examples, the pressure sensor can be used as a respiration sensor, configured to detect respiration rate, tidal volume, and phase. For example, respiration variation can be detected using the pressure sensor to determine the respiratory rate and tidal volume for patient management, rate-responsive therapies, etc.

In other examples, the device can include different signal pathways for detecting different physiologic information. For example, the device (e.g., an LCP device, etc.) can include a low-frequency, low-gain detection path for detecting pressure in an atrium or a ventricle, and a higher-frequency, higher-gain detection path for certain other measurements (e.g., body sounds, respiratory sounds, etc.). To save power, the device can switch to the higher-gain detection path only as necessary and under certain conditions (e.g., detected using the low-gain detection path, or one or more electrodes or other sensors, etc.).

FIG. 1 illustrates generally an example system 100 including first and second leadless cardiac pacemakers (LCP) devices 101, 102 positioned in left and right ventricles 114, 110 of a heart 104, respectively. In an example, the first and second LCP devices 101, 102 can communicate between each other using respective telemetry circuits, to one or more other LCP devices, to an implantable medical device (IMD) 106 (e.g., a subcutaneous cardiac rhythm management (CRM) device, a dedicated communication circuit, etc.), or directly to an external device, such as an external programmer 108, etc.

In other examples, the system 100 can include a single LCP device, two or more LCP devices, or one or two or more other implantable or insertable medical devices for placement in or on any chamber of the heart, including one or more of a left atrium 112, a right atrium 116, the left ventricle 114, or the right ventricle 110, delivered through the circulatory system of the heart 104 to a location of interest, implanted through the epicardium 118 or endocardium 120 and into the myocardium 122, or located near any chamber of the heart, such as in a pulmonary artery or other portion of the circulatory system of the heart 104.

In an example, the IMD 106 can include a leadless implanted device configured to communicate with one or more of the LCP devices 101, 102, or the IMB 106 can include one or more leads configured to be placed at various locations in the heart, working together with the one or more LCP devices. For example, the IMB 106 can include one or more sensors configured to provide information to one or more of the LCP devices 101, 102. In other examples, one or more of the LCP devices 101, 102 can be configured to supplement sensing in the IMB 106. For example, the IMD 106 can include a CRM device having an accelerometer. In certain examples, one or more of the pressure sensors of the LCP devices 101, 102 can be configured to supplement (e.g., acting as a hydrophone, or a sound pressure sensor) the detected accelerometer signal from the CRM device, such as to enhance detection of one or more physiologic signals, such as heart sounds, or one or more body sounds of the patient.

Figure 2:
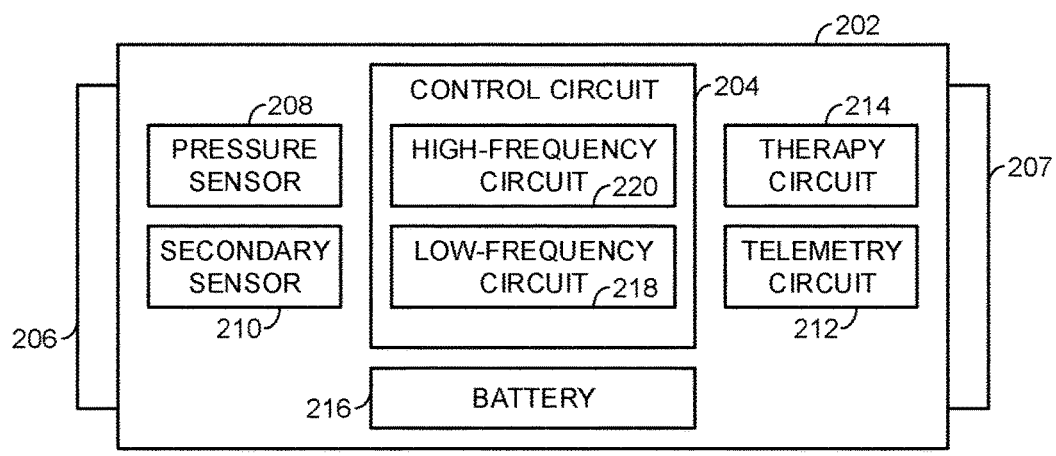
FIG. 2 illustrates generally an example leadless cardiac pacemaker (LCP) device including a control circuit, first and second electrodes, and a pressure sensor.

FIG. 2 illustrates generally an example leadless cardiac pacemaker (LCP) device 202 including a control circuit 204, first and second electrodes 206, 207, and a pressure sensor 208. In certain examples, the LCP device 202 can include more than two electrodes. The first and second electrodes 206, 207 can be configured to receive electrical information from, or provide a therapy or stimulation to, a heart of a patient. In certain examples, the first and second electrodes 206, 207 can be coupled to the control circuit 204, to a secondary sensor 210, to the therapy circuit 214, or to one or more other components of the LCP device 202.

The pressure sensor 208 can be configured to sense physiologic information from the patient, such as pressure or body sound information (e.g., including murmurs, valve openings or closures, respiratory sounds, etc.). The pressure sensor 208 can be coupled to the control circuit 204, and can receive control signals to operate one or more aspects of the pressure sensor 208, such as sampling frequency, signal resolution, etc. The control circuit 204 can be configured to receive information from the pressure sensor 208, the secondary sensor 210, the first and second electrodes 206, 207, the telemetry circuit 212 (e.g., information from a coupled IMB or external programmer, etc.), internal memory (not shown). The control circuit 204 can be configured to control the pressure sensor 208, the secondary sensor 210, the telemetry circuit 212, the therapy circuit 214, or one or more other component of the LCP device 202.

Depending on the control signals received from the control circuit 204, the pressure sensor 208 can alter one or more sensing property to efficiently detect specific physiologic signals or features. For example, as described above, the pressure sensor 208 can be configured to detect a pressure signal from the patient in a first mode (e.g., low-frequency mode), and can be configured to detect body sounds from the patient in a second mode (e.g., high-frequency mode). In an example, in the second mode, one or more of the power for sensing, the sampling frequency, signal resolution, amount of processing for filtering, etc., for the pressure sensor 208 can be increased. In the first mode, sensing can be configured for device longevity. Although described here as first and second modes, it is understood that a number of intermediate modes can be used to balance accurate detection of physiologic signals with power consumption, etc.

The telemetry circuit 212 can be configured to communicate information from the LCP device 202 to one or more other LCP devices, a subcutaneous IMD, an external programmer, or one or more other devices, or to receive information therefrom. In certain examples, the telemetry circuit 212 can be configured to receive information from one or more other implanted device, such as to provide the control signal to the pressure sensor. For example, an implantable CRM device can monitor one or more physiologic conditions, provide information to the LCP device 202 as to when the pressure sensor 208 should switch from the first state (e.g., low-frequency mode) to the second state (e.g., high-frequency mode), or to one or more intermediate states. Once the LCP device 202 has detected body sound information from its location, it can send that information to one or more other implanted devices, or external to the body, as desired.

Further, the LCP device 202 includes a battery 216 configured to power the circuits, sensors, and operations of the LCP device 202. In certain examples, the battery life of LCP devices 202 can rival that of current subcutaneous IMDs.

Although illustrated in FIG. 2 as an LCP device, in other examples, the LCP device 202 can include one or more other implantable or insertable medical devices.

Figure 3:
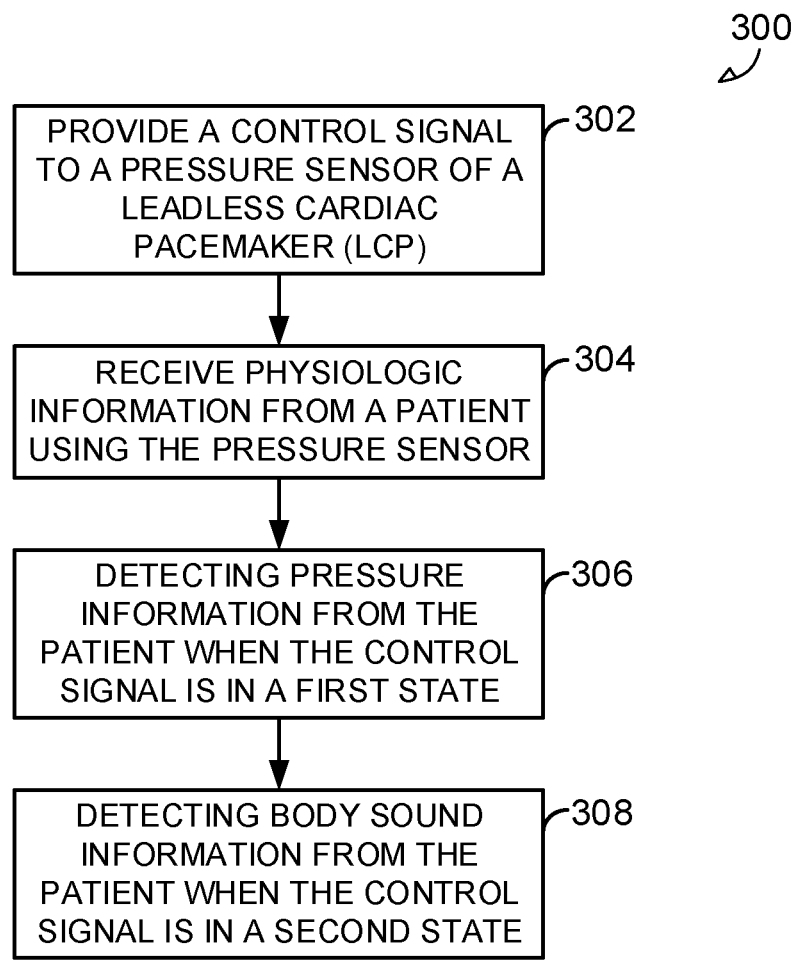
FIG. 3 illustrates generally an example method for detecting pressure and body sound information from a patient using a pressure sensor of a leadless cardiac pacemaker (LCP) device

FIG. 3 illustrates generally an example method 300 for detecting pressure and body sound information from a patient using a pressure sensor, such as a pressure sensor of a leadless cardiac pacemaker (LCP) or other implantable or insertable medical device.

At 302, a control signal can be provided to a pressure sensor of an LCP or other implantable or insertable medical device. A control circuit can provide the control signal using, in certain examples, information from the pressure sensor, one or more electrodes, or a secondary sensor of the LCP or other implantable or insertable medical device. In other examples, the LCP or other implantable or insertable medical device can be configured to receive information from another device using a telemetry circuit, and can provide the control signal using received information.

At 304, physiologic information can be received from a patient using the pressure sensor. The pressure sensor can be configured to operate in one of a plurality of modes, for example, depending on the control signal from the control circuit.

At 306, pressure information from the patient can be detected using the physiologic information received by the pressure sensor when the control signal is in a first state, such as by using a low-frequency data processing circuit in the control circuit. In an example, the low-frequency data processing circuit can include a normal operation of the LCP or other implantable or insertable medical device, configured for longevity of the battery of the device, etc.

At 308, body sound information can be detected from the patient using the physiologic information received by the pressure sensor when the control signal is in a second state, such as by using a high-frequency data processing circuit in the control circuit. In an example, the control circuit can be configured to provide the control signal to the pressure sensor in response to an expected detection window or period in which the data could be useful (e.g., detecting respiratory sounds during diastole to take advantage of lower noise levels, etc.).

Figure 4:
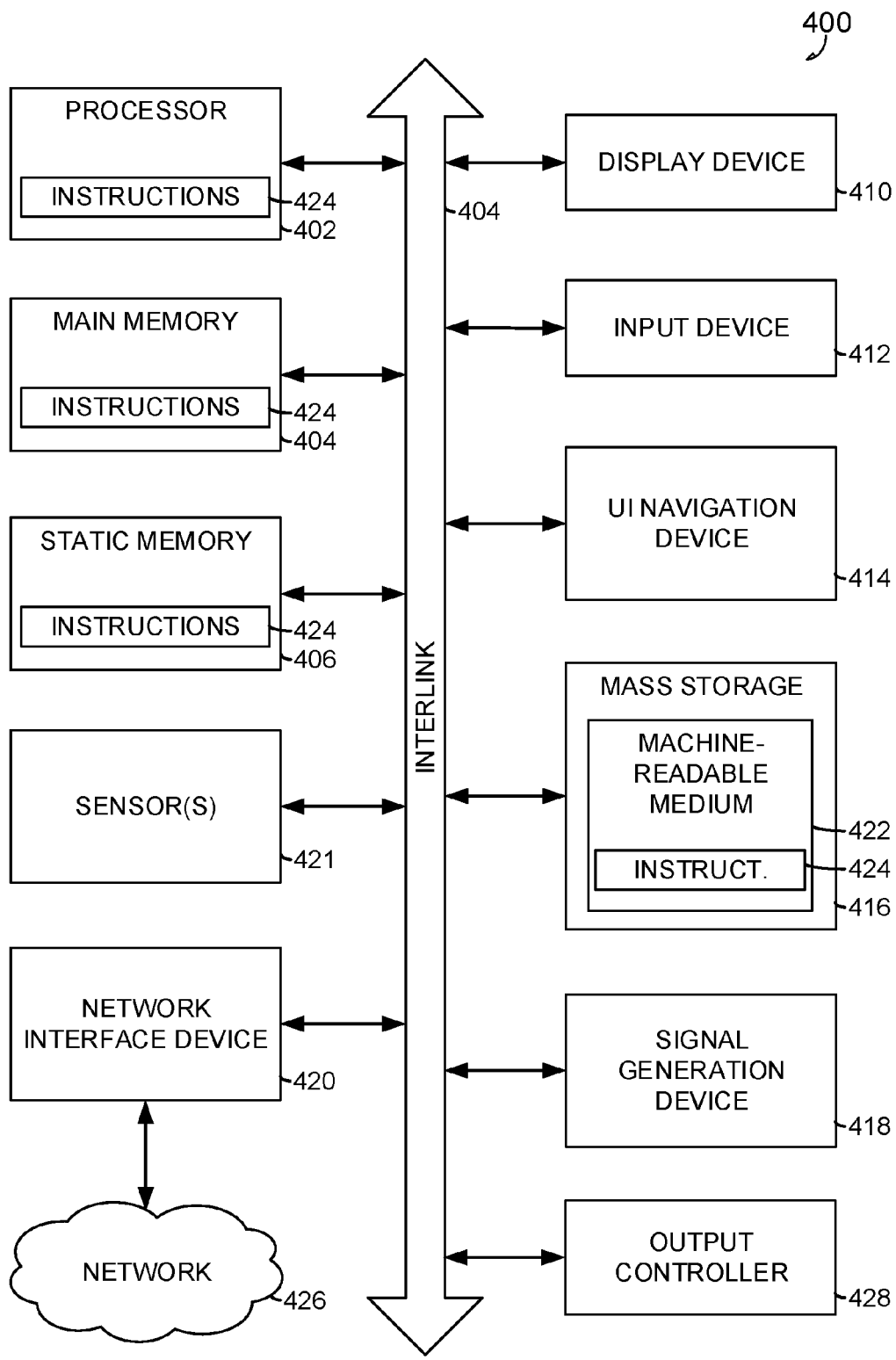
FIG. 4 illustrates generally a block diagram of an example machine upon which any one or more of the techniques (e.g., methodologies) discussed herein may perform.

FIG. 4 illustrates generally a block diagram of an example machine 400 upon which any one or more of the techniques (e.g., methodologies) discussed herein may perform. Portions of this description may be applicable to the computing framework of various portions of the LCP or other implantable or insertable medical device, or the external programmer. In alternative embodiments, the machine 400 may operate as a standalone device or may be connected (e.g., networked) to other machines. In a networked deployment, the machine 400 may operate in the capacity of a server machine, a client machine, or both in server-client network environments. In an example, the machine 400 may act as a peer machine in peer-to-peer (P2P) (or other distributed) network environment. The machine 400 may be a personal computer (PC), a tablet PC, a set-top box (STB), a personal digital assistant (PDA), a mobile telephone, a web appliance, a network router, switch or bridge, or any machine capable of executing instructions (sequential or otherwise)

that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 400 may include a hardware processor 402 (e.g., a central processing unit (CPU), a graphics processing unit (GPU), a hardware processor core, or any combination thereof), a main memory 404 and a static memory 406, some or all of which may communicate with each other via an interlink (e.g., bus) 408. The machine 400 may further include a display unit 410 (e.g., a raster display, vector display, holographic display, etc.), an alphanumeric input device 412 (e.g., a keyboard), and a user interface (UI) navigation device 414 (e.g., a mouse). In an example, the display unit 410, input device 412 and UI navigation device 414 may be a touch screen display. The machine 400 may additionally include a storage device (e.g., drive unit) 416, a signal generation device 418 (e.g., a speaker), a network interface device 420, and one or more sensors 421, such as a global positioning system (GPS) sensor, compass, accelerometer, or other sensor. The machine 400 may include an output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 416 may include a machine readable medium 422 on which is stored one or more sets of data structures or instructions 424 (e.g., software) embodying or utilized by any one or more of the techniques or functions described herein. The instructions 424 may also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, and/or associated caches and servers) configured to store the one or more instructions 424.

The term "machine readable medium" may include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 424 may further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 420 may include one or more physical jacks (e.g., Ethernet, coaxial, or phone jacks) or one or more antennas to connect to the communications network 426. In an example, the network interface device 420 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 400, and includes digital or analog communications signals or other intangible medium to facilitate communication of such software.

Additional Notes

An example (e.g., "Example 1") of subject matter (e.g., a system) may include a pressure sensor configured to receive physiologic information from a patient and a control circuit, coupled to the pressure sensor, configured to receive information from the pressure sensor, and to provide a control signal to the pressure sensor, wherein the control circuit includes a low-frequency data processing circuit configured to detect pressure information from the patient using the physiologic information received by the pressure sensor when the control signal is in a first state and a high-frequency data processing circuit configured to detect body sound information from the patient using the physiologic information received by the pressure sensor when the control signal is in a second state.

In Example 2, the subject matter of Example 1 may optionally include a leadless cardiac pacemaker (LCP), the LCP optionally including the pressure sensor, the pressure sensor optionally including a deformable element, the LCP optionally including an anchor to secure the LCP in an atrium or a ventricle of a heart of the patient and first and second electrodes configured to detect electrical information of the heart.

In Example 3, the subject matter of any one or more of Examples 1-2 may optionally be configured such that the control circuit is configured to provide the control signal in response to the detected electrical information.

In Example 4, the subject matter of any one or more of Examples 1-3 may optionally be configured such that the control circuit is configured to provide the control signal in response to the received physiologic information from the pressure sensor.

In Example 5, the subject matter of any one or more of Examples 1-4 may optionally be configured such that the control circuit is configured to detect diastole in the patient using information from the pressure sensor, and the control circuit is configured to provide the control signal in the second state when diastole is detected.

In Example 6, the subject matter of any one or more of Examples 1-5 may optionally be configured such that the LCP includes a secondary physiologic sensor configured to receive secondary physiologic information from the patient, and the control circuit is configured to provide the control signal in response to the secondary physiologic information detected from the secondary physiologic sensor.

In Example 7, the subject matter of any one or more of Examples 1-6 may optionally be configured such that the secondary sensor includes a respiration sensor configured to detect a respiration phase of the patient, and the control circuit is configured to provide the control signal in response to the detected respiration phase.

In Example 8, the subject matter of any one or more of Examples 1-7 may optionally be configured such that the pressure sensor is configured to sample physiologic information from the patient using the pressure sensor at a first sampling rate when the control signal is in the first state, and to sample physiologic information from the patient using the pressure sensor at a second sampling rate higher than the first sampling rate when the control signal is in the second state.

In Example 9, the subject matter of any one or more of Examples 1-8 may optionally be configured such that the body sound information includes information about at least one of a cardiac murmur, a respiratory sound, mitral regurgitation, or mitral stenosis detected using the physiologic information received by the pressure sensor when the control signal is in the second state.

An example (e.g., "Example 10") of subject matter (e.g., a method) may include providing a control signal to a pressure sensor of a leadless cardiac pacemaker (LCP) using a control circuit, receiving physiologic information from a patient using the pressure sensor, detecting pressure information from the patient using the physiologic information received by the pressure sensor when the control signal is in a first state using a low-frequency data processing circuit, and detecting body sound information from the patient using the physiologic information received by the pressure sensor when the control signal is in a second state using a high-frequency data processing circuit.

In Example 11, the subject matter of Example 10 may optionally include detecting electrical information of the patient using first and second electrodes, wherein the pressure sensor includes a deformable element, receiving physiologic information from the patient includes receiving physiologic information from within a left ventricle of a heart of the patient, and providing the control signal includes in response to the detected electrical information or in response to the received physiologic information from the pressure sensor.

In Example 12, the subject matter of any one or more of Examples 10-11 may optionally include detecting diastole in the patient using information from the pressure sensor, wherein providing the control signal includes in the second state when diastole is detected.

In Example 13, the subject matter of any one or more of Examples 10-12 may optionally include receiving secondary physiologic information from the patient using a secondary physiologic sensor, wherein providing the control signal includes in response to the secondary physiologic information detected from the secondary physiologic sensor.

In Example 14, the subject matter of any one or more of Examples 10-13 may optionally be configured such that receiving secondary physiologic information includes receiving a respiratory phase of the patient from a respiration sensor, and providing the control signal includes in response to the detected respiration phase.

In Example 15, the subject matter of any one or more of Examples 10-14 may optionally include sampling physiologic information from the patient using the pressure sensor at a first sample rate when the control signal is in the first state, and sampling physiologic information from the patient using the pressure sensor at a second sampling rate higher than the first sampling rate when the control signal is in the second state, wherein detecting body sound information includes detecting information about at least one of a cardiac murmur, a respiratory sound, mitral regurgitation, or mitral stenosis detected using the physiologic information received by the pressure sensor when the control signal is in the second state.

An example (e.g., "Example 16") of subject matter (e.g., a system) may include a leadless cardiac pacemaker (LCP), including a pressure sensor configured to receive physiologic information from a patient, and a control circuit, coupled to the pressure sensor, configured to receive information from the pressure sensor, and to provide a control signal to the pressure sensor, wherein the control circuit includes a low-frequency data processing circuit configured to detect pressure information from the patient using the physiologic information received by the pressure sensor when the control signal is in a first state, and a high-frequency data processing circuit configured to detect body sound information from the patient using the physiologic information received by the pressure sensor when the control signal is in a second state.

In Example 17, the subject matter of Example 16 may optionally be configured such that the pressure sensor includes a deformable element, and the LCP includes an anchor to secure the LCP in an atrium or a ventricle of a heart of the patient, and first and second electrodes configured to detect electrical information of the heart.

In Example 18, the subject matter of any one or more of Examples 16-17 may optionally be configured such that the LCP includes an anchor configured to secure the LCP to an interior wall of a left ventricle of a heart, and first and second electrodes configured to detect electrical information of the heart.

In Example 19, the subject matter of any one or more of Examples 16-18 may optionally be configured such that the control circuit is configured to provide the control signal in response to the detected electrical information.

In Example 20, the subject matter of any one or more of Examples 16-19 may optionally be configured such that the control circuit is configured to provide the control signal in response to the received physiologic information from the pressure sensor.

In Example 21, the subject matter of any one or more of Examples 16-20 may optionally be configured such that the control circuit is configured to detect diastole in the patient using information from the pressure sensor, and the control circuit is configured to provide the control signal in the second state when diastole is detected.

In Example 22, the subject matter of any one or more of Examples 16-21 may optionally be configured such that the control circuit is configured to provide the control signal in the second state when the information from the pressure sensor drops below a threshold.

In Example 23, the subject matter of any one or more of Examples 16-22 may optionally be configured such that the LCP includes a secondary physiologic sensor configured to receive secondary physiologic information from the patient, and the control circuit is configured to provide the control signal in response to the secondary physiologic information detected from the secondary physiologic sensor.

In Example 24, the subject matter of any one or more of Examples 16-23 may optionally be configured such that the secondary sensor includes a respiration sensor configured to detect a respiration phase of the patient, and the control circuit is configured to provide the control signal in response to the detected respiration phase.

In Example 25, the subject matter of any one or more of Examples 16-24 may optionally be configured such that the pressure sensor is configured to sample physiologic information from the patient using the pressure sensor at a first sampling rate when the control signal is in the first state, and to sample physiologic information from the patient using the pressure sensor at a second sampling rate higher than the first sampling rate when the control signal is in the second state.

In Example 26, the subject matter of any one or more of Examples 16-25 may optionally be configured such that the body sound information includes information about at least one of a cardiac murmur, a respiratory sound, mitral regurgitation, or mitral stenosis detected using the physiologic information received by the pressure sensor when the control signal is in the second state.

An example (e.g., "Example 27") of subject matter (e.g., a method) may include providing a control signal to a pressure sensor of a leadless cardiac pacemaker (LCP) using a control circuit, receiving physiologic information from a patient using the pressure sensor, detecting pressure information from the patient using the physiologic information received by the pressure sensor when the control signal is in a first state using a low-frequency data processing circuit, and detecting body sound information from the patient using the physiologic information received by the pressure sensor when the control signal is in a second state using a high-frequency data processing circuit.

In Example 28, the subject matter of Example 27 may optionally include detecting electrical information of the patient using first and second electrodes, wherein the pressure sensor includes a deformable element, and receiving physiologic information from the patient includes receiving physiologic information from within a left ventricle of a heart of the patient.

In Example 29, the subject matter of any one or more of Examples 27-28 may optionally be configured such that providing the control signal includes in response to the detected electrical information.

In Example 30, the subject matter of any one or more of Examples 27-29 may optionally be configured such that providing the control signal includes in response to the received physiologic information from the pressure sensor.

In Example 31, the subject matter of any one or more of Examples 27-30 may optionally include detecting diastole in the patient using information from the pressure sensor, wherein providing the control signal includes providing the control signal in the second state when diastole is detected.

In Example 32, the subject matter of any one or more of Examples 27-31 may optionally include receiving secondary physiologic information from the patient using a secondary physiologic sensor, wherein providing the control signal includes in response to the secondary physiologic information detected from the secondary physiologic sensor.

In Example 33, the subject matter of any one or more of Examples 27-32 may optionally include receiving a respiratory phase of the patient from a respiration sensor, wherein providing the control signal includes in response to the detected respiration phase.

In Example 34, the subject matter of any one or more of Examples 27-33 may optionally include sampling physiologic information from the patient using the pressure sensor at a first sample rate when the control signal is in the first state, and sampling physiologic information from the patient using the pressure sensor at a second sampling rate higher than the first sampling rate when the control signal is in the second state.

In Example 35, the subject matter of any one or more of Examples 27-34 may optionally be configured such that detecting body sound information includes detecting information about at least one of a cardiac murmur, a respiratory sound, mitral regurgitation, or mitral stenosis detected using the physiologic information received by the pressure sensor when the control signal is in the second state.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   a pressure sensor configured to receive physiologic information from a patient; and
   a control circuit, coupled to the pressure sensor, configured to receive information from the pressure sensor, and to control a state of the pressure sensor, wherein the control circuit is configured to:
   detect pressure information from the patient using the physiologic information received by the pressure sensor in a first state; and
   detect body sound information from the patient using the physiologic information received by the pressure sensor in a second state.

2. The system of claim 1, including a leadless cardiac pacemaker (LCP), wherein the LCP includes the pressure sensor having a deformable element, and wherein the LCP includes first and second electrodes configured to detect electrical information of the heart.

3. The system of claim 1, including a leadless cardiac pacemaker (LCP), wherein the LCP includes first and second electrodes configured to detect electrical information of the heart.

4. The system of claim 3, wherein the control circuit is configured to control the state of the pressure sensor using the detected electrical information.

5. The system of claim 1, wherein the control circuit is configured to control the state of the pressure sensor using the received physiologic information from the pressure sensor.

6. The system of claim 5, wherein the control circuit is configured to detect diastole in the patient using information from the pressure sensor, and
   wherein the control circuit is configured to control the state of the pressure sensor using the detected diastole.

7. The system of claim 5, wherein the control circuit is configured to place the pressure sensor in the second state when the information from the pressure sensor is below a threshold.

8. The system of claim 1, including a secondary physiologic sensor configured to receive secondary physiologic information from the patient, and
   wherein the control circuit is configured to control the state of the pressure sensor using the secondary physiologic information detected from the secondary physiologic sensor.

9. The system of claim 8, wherein the secondary sensor includes a respiration sensor configured to detect a respiration phase of the patient, and
   wherein the control circuit is configured to control the pressure sensor using the detected respiration phase.

10. The system of claim 1, wherein the pressure sensor is configured to sample physiologic information from the patient using the pressure sensor at a first sampling rate in the first state, and to sample physiologic information from the patient using the pressure sensor at a second sampling rate higher than the first sampling rate in the second state.

11. The system of claim 1, wherein the body sound information includes information about at least one of a cardiac murmur, a respiratory sound, mitral regurgitation, or mitral stenosis detected using the physiologic information received by the pressure sensor in the second state.

12. A method, comprising:
controlling a state of a pressure sensor using a control circuit;
receiving physiologic information from a patient using the pressure sensor;
detecting pressure information from the patient using the physiologic information received by the pressure sensor in a first state using the control circuit; and
detecting body sound information from the patient using the physiologic information received by the pressure sensor in a second state using a the control circuit.

13. The method of claim 12, including:
detecting electrical information of the patient using first and second electrodes,
wherein the pressure sensor includes a deformable element, and
wherein the receiving physiologic information from the patient includes receiving physiologic information from within a left ventricle of a heart of the patient.

14. The method of claim 13, wherein the controlling the state of the pressure sensor includes using the detected electrical information.

15. The method of claim 12, wherein the controlling the state of the pressure sensor includes using the received physiologic information from the pressure sensor.

16. The method of claim 15, including:
detecting diastole in the patient using information from the pressure sensor,
wherein the controlling the state of the pressure sensor includes using the detected diastole.

17. The method of claim 12, including:
receiving secondary physiologic information from the patient using a secondary physiologic sensor,
wherein the controlling the state of the pressure sensor includes using the secondary physiologic information detected from the secondary physiologic sensor.

18. The method of claim 17, wherein the receiving secondary physiologic information includes:
receiving a respiratory phase of the patient from a respiration sensor,
wherein controlling the state of the pressure sensor includes using the detected respiration phase.

19. The method of claim 12, including:
sampling physiologic information from the patient using the pressure sensor at a first sample rate in the first state; and
sampling physiologic information from the patient using the pressure sensor at a second sampling rate higher than the first sampling rate in the second state.

20. The method of claim 12, wherein the detecting body sound information includes detecting information about at least one of a cardiac murmur, a respiratory sound, mitral regurgitation, or mitral stenosis detected using the physiologic information received by the pressure sensor in the second state.

* * * * *